US006849428B1

(12) United States Patent
Evans et al.

(10) Patent No.: US 6,849,428 B1
(45) Date of Patent: Feb. 1, 2005

(54) INTEIN-MEDIATED PROTEIN LIGATION OF EXPRESSED PROTEINS

(75) Inventors: Thomas C. Evans, Somerville, MA (US); Ming-Qun Xu, Hamilton, MA (US); Shaorong Chong, Cambridge, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/249,543

(22) Filed: Feb. 12, 1999

Related U.S. Application Data

(63) Continuation-in-part of application No. 08/811,492, filed on Mar. 5, 1997, now Pat. No. 5,834,247.
(60) Provisional application No. 60/102,413, filed on Sep. 30, 1998.

(51) Int. Cl.[7] .................. C12N 15/62; C12N 15/74; C12N 15/79; C07K 19/00
(52) U.S. Cl. ............... 435/69.7; 435/68.1; 435/252.3; 435/320.1; 435/471; 530/350
(58) Field of Search .................... 435/69.7, 68.1, 435/252.3, 320.1, 471, 69.1, 67.7; 530/350, 402; 536/23.4

(56) References Cited

U.S. PATENT DOCUMENTS

| | | | | | |
|---|---|---|---|---|---|
| 5,496,714 | A | * | 3/1996 | Comb et al. | 435/69.7 |
| 5,777,077 | A | * | 7/1998 | Albericio et al. | 530/335 |
| 5,795,731 | A | * | 8/1998 | Belfort | 435/32 |
| 5,834,247 | A | * | 11/1998 | Comb et al. | 435/69.7 |
| 6,045,774 | A | * | 4/2000 | Hiatt et al. | 424/91.1 |
| 6,168,784 | B1 | * | 1/2001 | Offord et al. | 424/85.1 |
| 6,184,344 | B1 | * | 2/2001 | Kent et al. | 530/323 |
| 6,217,881 | B1 | * | 4/2001 | Stevens | 424/195.11 |
| 6,310,180 | B1 | * | 10/2001 | Tam | 530/339 |
| 6,326,468 | B1 | * | 12/2001 | Canne et al. | 530/333 |

OTHER PUBLICATIONS

Canne, L.E., et al., 1996, "Extending the applicability of native chemical ligation", Journal of the American Chemical Society, vol. 118, pp. 5891–5896.*
Nilsson, B. L., et al, 2000, "Staudinger ligation: A peptide from a thioster and azide", Organic Letters, vol. 0, pp. A–C.*
Hondal, R.J., et al., 2001, "Selenocysteine in native chemical ligation and expressed protein synthesis", Jounral of the American Chemical Society, vol. 123, pp. 5140–5141.*
Bock, A., et al., 1991, "Selenocysteine: the 21st amino acid", Molecular Biology, vol. 5, pp. 515–520.*
Muller, S., et al., 1994, "The formation of diselenide bridges in proteins by incorporation of selenocysteine residues: Biosyntheses and characterization of (Se)2–thioredoxin", Biochemistry, vol. 33, pp. 3404–3412.*
Evans, T.C. et al., 1999, "The cyclization and polymerization of bacterially expressed proteins using modified self–splicing inteins", The Journal of Biological Chemistry, vol. 274, pp. 18359–18363.*
Dawson, P. E., et al., 1994, "Synthesis of proteins by native chemical ligation", Science, vol. 266, pp. 776–779.*
Telenti, A., et al., 1997, "The Mycobacterium xenopi GyrA protein splicing element: Characterization of a minimal intein", Journal of Bacteriology, vol. 179, pp. 6378–6382.*
Mills, K. V., et al., 1998, "Protein splicing in trans by purified N– and C–terminal fragments of the Mycobacterium tuberculosis RecA intein", Proceedings of the National Academy of Sciences, U.S.A., vol. 95, pp. 3543–3548.*
Severino, K., et al., 1998, "Expressed protein ligation, a novel method for studying protein–protein interactions in transcription", The Journal of Biological Chemistry, vol. 273, pp. 16205–16209.*
Perler, et al., Nucl. Acids Res. 22:1125–1127 (1994).
Perler, et al., Curr. Opin. Chem. Biol. 1:1292–299 (1997).
Perler, et al., Cell 92(1):1–4 (1998).
Xu, et al., EMBO J. 15(19)5146–5153 (1996).
Chong, et al., Gene 192:271–281 (1997).
Evans, et al. Protein Sci. 7:2256–2264 (1998).
Muir, et al., PNAS USA 95:6705–6710 (1998).
Xu, et al., PNAS USA 96:388–393 (1999).
Erlandson, et al. Chem. Biol., 3:981–991 (1996).
Perler, et al., Nucl. Acids Res. 27:346–347 (1999).
Smith, et al., J. Bacteriol., 179:7135–7155 (1997).
Chong, et al., J. Biol. Chem., 273:10567–10577 (1998).

* cited by examiner

*Primary Examiner*—Ponnathapura Achutamurthy
*Assistant Examiner*—William W. Moore
(74) *Attorney, Agent, or Firm*—Harrier M. Strimpel

(57) ABSTRACT

A method for the ligation of expressed proteins which utilizes inteins, for example the RIR1 intein from *Methanobacterium thermotrophicum*, is provided. Constructs of the Mth RIR1 intein in which either the C-terminal asparagine or N-terminal cysteine of the intein are replaced with alanine enable the facile isolation of a protein with a specified N-terminal, for example, cysteine for use in the fusion of two or more expressed proteins. The method involves the steps of generating a C-terminal thioester-tagged target protein and a second target protein having a specified N-terminal via inteins, such as the modified Mth RIR1 intein, and ligating these proteins. A similar method for producing a cyclic or polymerized protein is provided. Modified inteins engineered to cleave at their C-terminus or N-terminus, respectively, and DNA and plasmids encoding these modified inteins are also provided.

24 Claims, 4 Drawing Sheets

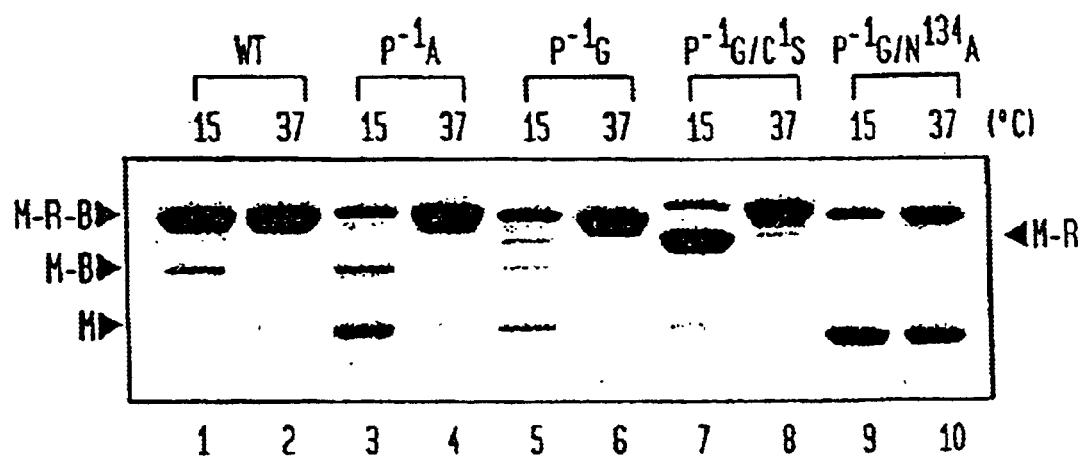

FIG. 4

```
  1 CAACTCGGGAGGATAGAGGCAACCAACCCCTGTGTATCCGGTGACACCAT  50
    |  ||||||||||||||| |||||||||||||||||
  1 ..........CTCGAGGCAACCAACCCCTGCGTATCCGGTGACACCAT  38

51 TGTAATGACATCCGGGGGTCCGCGGACAGTGGCTGAACTGGAGGGCAAGC 100
    ||||||||   || |||||||| || ||||||||||||||||||||| |
 39 TGTAATGACTAGTGGCGGTCCGCGCACTGTGGCTGAACTGGAGGGCAAAC  88

101 CCTTCACCGCACTTATCAGGGGCTCAGGGTACCCTGCCCCTCAGGTTTC 150
    | ||||||||| ||  | ||||| || |||||  ||||||||||||||
 89 CGTTCACCGCACTGATTCGCGGCTCTGGCTACCCATGCCCCTCAGGTTTC 138

151 TTCAGGACCTGTGAACGGGACGTATATGATCTTAGAACCAGGGAGGGTCA 200
    ||| | |||||||||||| |||||||||||||  | |  | |||||||
139 TTCCGCACCTGTGAACGTGACGTATATGATCTGCGTACACGTGAGGGTCA 188

201 TTGCTTAAGGTTGACCCATGATCACAGGGTCCTTGTAATGGATGGTGGTC 250
    ||||||| | |||||||||||||||| || || || ||.|||||||| |
189 TTGCTTACGTTTGACCCATGATCACCGTGTTCTGGTGATGGATGGTGGCC 238

251 TGGAATGGCGTGCCGCCGGTGAACTTGAAAGGGGAGACCGCCTTGTGATG 300
    |||||||||||||||| ||| ||||||  | | |||||||| ||||||
239 TGGAATGGCGTGCCGCGGGTGAACTGGAACGCGGCGACCGCCTGGTGATG 288

301 GATGATGCTGCAGGGGAGTTTCCGGCACTTGCAACCTTCAGAGGCCTCAG 350
    ||||||| || || ||||||||||||||| |||||||| | |||| |
289 GATGATGCAGCTGGCGAGTTTCCGGCACTGGCAACCTTCCGTGGCCTGCG 338

351 GGGCGCCGGCCGCCAGGATGTCTATGACGCCACTGTCTACGGTGCCAGTG 400
    |||||  |||||||||||||| | ||||||| |||| | |||||| | |
339 TGGCGCTGGCCGCCAGGATGTTTATGACGCTACTGTTTACGGTGCTAGCG 388

401 CATTCACAGCCAATGGATTCATAGTCCACAACTGTGGGGAGCAGCCACTC 450
    |||||| || |||||||| || || ||||||||||| ||||||||| |
389 CATTCACTGCTAATGGCTTCATTGTACACAACTGTGGCGAGCAGCCAACC 438

451 CTCACCCATGAA 462

439 GGTGAATTC... 447
```

INTEIN-MEDIATED PROTEIN LIGATION OF EXPRESSED PROTEINS

RELATED APPLICATIONS

This Application gains priority from U.S. Provisional Application Ser. No. 60/102,413 filed Sep. 30, 1998, entitled "Intein Mediated Peptide Ligation." This appln is also a CIP of Ser No. 08/811,492 filed Mar. 5, 1997 now U.S. Pat No 5,834,247.

BACKGROUND OF THE INVENTION

The present invention relates to methods of intein-mediated ligation of proteins. More specifically, the present invention relates to intein-mediated ligation of expressed proteins containing a predetermined N-terminal residue and/or a C-terminal thioester generated via use of one or more naturally occurring or modified inteins. Preferably, the predetermined residue is cysteine.

Inteins are the protein equivalent of the self-splicing RNA introns (see Perler et al., *Nucleic Acids Res.* 22:1125–1127 (1994)), which catalyze their own excision from a precursor protein with the concomitant fusion of the flanking protein sequences, known as exteins (reviewed in Perler et al., *Curr. Opin. Chem. Biol.* 1:292–299 (1997); Perler, F. B. *Cell* 92(1):1–4 (1998); Xu et al., *EMBO J.* 15(19):5146–5153 (1996)).

Studies into the mechanism of intein splicing led to the development of a protein purification system that utilized thiol-induced cleavage of the peptide bond at the N-terminus of the *Sce* VMA intein (Chong et al., *Gene* 192(2):271–281 (1997)). Purification with this intein-mediated system generates a bacterially-expressed protein with a C-terminal thioester (Chong et al., (1997)). In one application, where it is described to isolate a cytotoxic protein, the bacterially expressed protein with the C-terminal thioester is then fused to a chemically-synthesized peptide with an N-terminal cysteine using the chemistry described for "native chemical ligation" (Evans et al., *Protein Sci.* 7:2256–2264 (1998); Muir et al., *Proc. Natl. Acad. Sci. USA* 95:6705–6710 (1998)).

This technique, referred to as "intein-mediated protein ligation" (IPL), represents an important advance in protein semi-synthetic techniques. However, because chemically-synthesized peptides of larger than about 100 residues are difficult to obtain, the general application of IPL is limited by the requirement of a chemically-synthesized peptide as a ligation partner.

IPL technology would be significantly expanded if an expressed protein with a predetermined N-terminus, such as cysteine, could be generated. This would allow the fusion of one or more expressed proteins from a host cell, such as bacterial, yeast or mammalian cells.

One method of generating an N-terminal cysteine is with the use of proteases. However, proteases have many disadvantages, such as the possibility of multiple protease sites within a protein, as well as the chance of non-specific degradation. Furthermore, following proteolysis, the proteases must be inactivated or purified away from the protein of interest before proceeding with IPL. (Xu, et al., *Proc. Natl. Acad. Sci. USA* 96(2):388–393 (1999) and Erlandson, et al., *Chem. Biol.*, 3:981–991 (1996))

There is, therefore, a need for an improved intein-mediated protein ligation method which overcomes the noted limitations of current IPL methods and which eliminates the need for use of proteases to generate an N-terminal cysteine residue. Such an improved IPL method would have widespread applicability for the ligation of expressed proteins, for example, labeling of extensive portions of a protein for, among other things, NMR analysis.

SUMMARY OF THE INVENTION

In accordance with the present invention, there is provided a method for the ligation of expressed proteins utilizing one or more inteins which display cleavage at their N- and/or C-termini. In accordance with the present invention, such inteins may occur either naturally or may be modified to cleave at their N- and/or C-termini. Inteins displaying N- and/or C-terminal cleavage enable the facile isolation of a protein having a C-terminal thioester and a protein having an N-terminal amino acid residue such as cysteine, respectively, for use in the fusion of one or more expressed proteins. Alternatively, the method may be used to generate a single protein having both a C-terminal thioester and a specified N-terminal amino acid residue, such as cysteine, for the creation of cyclic or polymerized proteins. These methods involve the steps of generating at least one C-terminal thioester-tagged first target protein, generating at least one second target protein having a specified N-terminal amino acid residue, for example cysteine, and ligating these proteins. This method may be used where a single protein is expressed, where, for example, the C-terminal thioester end of the protein is fused to the N-terminal end of the same protein. The method may further include chitin-resin purification steps.

In one preferred embodiment the intein from the RIR1 *Methanobacterium thermoautotrophicum* is modified to cleave at either the C-terminus or N-terminus. The modified intein allows for the release of a bacterially expressed protein during a one-column purification, thus eliminating the need proteases entirely. DNA encoding these modified inteins and plasmids containing these modified inteins are also provided by the instant invention.

BRIEF DESCRIPTION OF THE DRAWINGS

FIG. 3 is a gel depicting the effect of induction temperature on the cleaving and/or splicing activity of the Mth RIR1 intein or Mth RIR1 intein mutants. The Mth RIR1 intein or mutants thereof, with 5 native N- and C-terminal extein residues were induced at either 15° C. or 37° C. The intein was expressed as a fusion protein (M-R-B, 63 kDa) consisting of N-terminal maltose binding protein (M, 43 kDa), the Mth RIR1 intein (R, 15 kDa) and at its C-terminus was the chitin binding domain (B, 5 kDa). Lanes 1 and 2. M-R-B with the unmodified Mth RIR1 intein. Note the small amount of spliced product (M-B, 48 kDa). Lanes 3 and 4. Mth intein with $Pro^{-1}$ replaced with Ala, M-R-B($P^{-1}A$). Both spliced product (M-B) and N-terminal cleavage product (M) are visible. Lanes 5 and 6. Replacement of $Pro^{-1}$ with Gly (M-R-B($P^{-1}G$)) showed some splicing as well as N- and C-terminal cleavage, M and M-R, respectively. Lanes 7 and 8. The $Pro^{-1}$ to Gly and $Cys^{1}$ to Ser double mutant, M-R-B($P^{-1}G/C^{1}S$), displayed induction temperature dependent C-terminal cleavage (M-R) activity. Lanes 9 and 10. The M-R-B($P^{-1}G/N^{134}A$) mutant possessed only N-terminal cleavage activity producing M. The Mth intein or Mth intein-CBD fusion is not visible in this Figure.

FIG. 4 is a nucleotide sequence (SEQ ID NO:23) comparison of wild type Mth RIR1 intein and synthetic Mth RIR1 intein indicating the location of 61 silent base mutations designed to increase expression in *E. coli*. DNA alignment of the wild type Mth RIR1 intein (top strand) and the synthetic Mth RIR1 intein (bottom strand). To increase expression levels in *E. coli*, 61 silent base changes were made in 49 separate codons when creating the synthetic gene. The first and last codons of the wild type Mth RIR1 intein are shown in bold.

DETAILED DESCRIPTION

Figure 1:
FIG. 1 is a diagram depicting both the N-terminal and C-terminal cleavage reactions which comprise intein-mediated protein ligation. The modified Mth RIR1 intein was used to purify both MBP with a C-terminal thioester and T4 DNA ligase with an N-terminal cysteine. The Mth RIR1 intein for N-terminal cleavage, intein(N), carried the $P^{-1}G/N^{134}A$ double mutation. The full length fusion protein consisting of MBP-intein(N)-CBD was separated from cell extract by binding the CBD portion of the fusion protein to a chitin resin. Overnight incubation in the presence of 100 mM 2-mercaptoethanesulfonic acid (MESNA) induced cleavage of the peptide bond prior to the N-terminus of the intein and created a thioester on the C-terminus of MBP. The C-terminal cleavage vector, intein(C), had the $P^{-1}G/C^{1}A$ double mutation. The precursor CBD-intein(C)-T4 DNA ligase was isolated from induced *E. coli* cell extract by binding to a chitin resin as described for N-terminal cleavage. Fission of the peptide bond following the C-terminal residue of the intein at a preferred temperature and pH resulted in the production of T4 DNA ligase with an N-terminal cysteine. Ligation occurred when the proteins containing the complementary reactive groups were mixed and concentrated, resulting in a native peptide bond between the two reacting species.
Figure 1:
Figure 1:
Figure 1:
Figure 1:
Figure 1:
Figure 1:
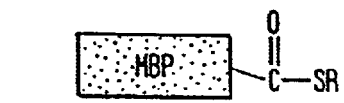
Figure 1:
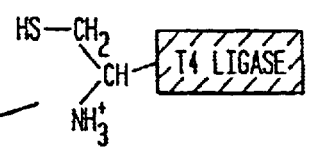
Figure 1:
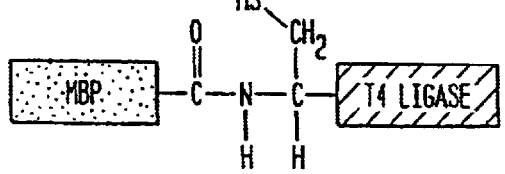

The present invention provides a solution to the limitations of current intein-mediated ligation methods by eliminating the need for a synthetic peptide as a ligation partner, and providing a method which is suitable for the fusion one or more expressed proteins.

In general, any intein displaying N- and/or C-terminal cleavage at its splice junctions can be used to generate a defined N-terminus, such as cysteine as well as a C-terminal thioester for use in the fusion of expressed proteins. Inteins which may be used in practicing the present invention include those described in Perler, et al., *Nucleic Acids Res.*, 27(1):346–347 (1999).

In accordance with one preferred embodiment, an intein found in the ribonucleoside diphosphate reductase gene of *Methanobacterium thermoautotrophicum* (the Mth RIR1 intein) was modified for the facile isolation of a protein with an N-terminal cysteine for use in the in vitro fusion of two bacterially-expressed proteins. The 134-amino acid Mth RIR1 intein is the smallest of the known mini-inteins, and may be close to the minimum amino acid sequence needed to promote splicing (Smith et. al., *J. Bacteriol.* 179: 7135–7155 (1997)).

The Mth RIR1 intein has a proline residue on the N-terminal side of the first amino acid of the intein. This residue was previously shown to inhibit splicing in the Sce VMA intein (Chong et al., *J. Biol. Chem.* 273:10567–10577 (1998)). The intein was found to splice poorly in *E. coli* when this naturally occurring proline is present. Splicing proficiency increases when this proline is replaced with an alanine residue. Constructs that display efficient N- and C-terminal cleavage are created by replacing either the C-terminal asparagine or N-terminal cysteine of the intein, respectively, with alanine.

These constructs allow for the formation of an intein-generated C-terminal thioester on a first target protein and an intein-generated N-terminal cysteine on a second target protein. These complementary reactive groups may then be ligated via native chemical ligation to produce a peptide bond (Evans et al supra (1998), Muir et al supra (1998)). Alternatively, a single protein containing both reactive groups may be generated for the creation of cyclic or polymerized proteins. Likewise, more than one first or second target proteins may be generated via use of multiple mutant inteins.

As used herein, the terms fusion and ligation are used interchangeably. Also as used herein, protein shall mean any protein, fragment of any protein, or peptide capable of ligation according to the methods of the instant invention. Further, as used herein, target protein shall mean any protein the ligation of which, according to the methods of the instant invention, is desired.

The general method of intein-mediated protein ligation in accordance with the present invention is as follows:

(1) An intein of interest is isolated and cloned into an appropriate expression vector(s) such as bacterial, plant, insect, yeast and mammalian cells.

(2) The intein is engineered for N- and/or C-terminal cleavage unless the wild type intein displays the desired cleavage activities. In a preferred embodiment, a modified intein with the desired cleavage properties can be generated by substituting one or more residues within and/or flanking the intein sequence. For example, a modified intein having N-terminal cleavage activity can be created by changing the last intein residue. Alternatively, a modified intein with C-terminal cleavage activity can be created by changing the first intein residue.

(3) The intein with N- and/or C-terminal cleavage activity is fused with an affinity tag to allow purification away from other endogenous proteins.

(4) The intein or inteins, either wild type or modified, that display N-terminal and/or C-terminal cleavage, or both, are fused to the desired target protein coding region or regions upstream and/or downstream of the intein.

(5) An intein that cleaves at its N-terminus in a thiol reagent dependent manner is used to isolate a protein with a C-terminal thioester. This cleavage and isolation is, for example, carried out as previously described for the Sce VMA and Mxe GyrA inteins (Chong et al., Gene 192(2):271–281 (1997); Evans et al., Protein Sci. 7:2256–2264 (1998)). As discussed previously, multiple C-terminal thioester-tagged proteins may be generated at this step.

(6) A target protein having a specified N-terminus is generated by cleavage of a construct containing an intein that cleaves at its C-terminus. The specified N-terminal residue may be any of the amino acids, but preferably cysteine. As discussed previously, this step may alternately generate a specified N-terminal on the same protein containing a C-terminal thioester, to yield a single protein containing both reactive groups. Alternatively, multiple proteins having the specified N-terminus may be generated at this step.

Figure 2A:
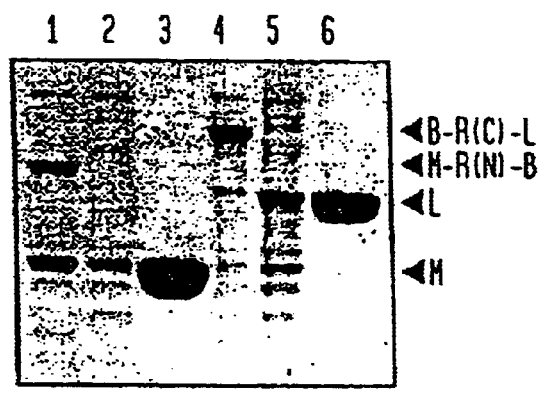
FIG. 2A is a gel depicting the purification of a C-terminal thioester-tagged maltose binding protein (MBP) via a thiol-inducible Mth RIR1 intein construct pMRB10G (containing the modified intein, R(N), with $P^{-1}G/N^{134}A$ mutation) and the purification of T4 DNA ligase having an N-terminal cysteine using the vector pBRL-A (containing the modified intein, R(C), with $P^{-1}G/C^{1}A$ mutation). Lanes 1–3, purification of maltose binding protein (MBP) (M, 43 kDa) with a C-terminal thioester. Lane 1. ER2566 cells transformed with plasmid pMRB10G following Isopropyl β-D-thiogalactopyranoside (IPTG) induction. Lane 2. Cell extract after passage over a chitin Ln resin. Note that the fusion protein, M-R(N)-B, binds to the resin, where B is the chitin binding domain. Lane 3. Fraction 3 of the elution from the chitin resin following overnight incubation at 4° C. in the presence of 100 mM MESNA. Lanes 4–6, purification of T4 DNA ligase (L, 56 kDa) with an N-terminal cysteine. Lane 4. IPTG induced ER2566 cells containing plasmid pBRL-A. Lane 5. Cell extract after application to a chitin resin. B-R(C)-L, the fusion protein, binds to the resin. Lane 6. Elution of T4 DNA ligase with an N-terminal cysteine after overnight incubation at room temperature in pH 7 buffer
Figure 2B:
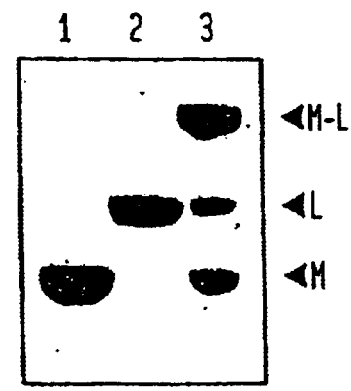
FIG. 2B is a gel depicting ligation of T4 DNA ligase having an N-terminal cysteine to a C-terminal thioester tagged MBP. Lane 1. Thioester-tagged MBP. Lane 2. T4 DNA ligase with an N-terminal cysteine. Lane 3. Ligation reaction of MBP (0.8 mM) with T4 DNA ligase (0.8 mM), generating M-L, after overnight incubation at 4° C.

(7) Thioester-tagged target protein and target protein having a specified N-termini are fused via intein-mediated protein ligation (IPL) (see FIG. 2B). In a preferred embodiment, the N-terminus is cysteine. Alternatively, a single protein containing both a C-terminal thioester and a specified N-terminus, such as a cysteine, may undergo intramolecular ligation to yield a cyclic product and/or intermolecular ligation to yield polymerized proteins.

The methodology described by the instant invention significantly expands the utility of current IPL methods to enable the labeling of extensive portions of a protein for NMR analysis and the isolation of a greater variety of cytotoxic proteins. In addition, this advance opens the possibility of labeling the central portion of a protein by ligating three or more fragments.

The use of an intein or inteins with N-terminal and C-terminal cleavage activity provides the potential to create a defined N-terminus, such as a cysteine, and a C-terminal thioester on a single protein. The intramolecular ligation of the resulting protein generates a circular protein, whereas the intermolecular ligation of several of these proteins generates a protein polymer.

Cleavage at the N- and/or the C-terminus of an intein can be brought about by introducing changes to the intein and/or its extein sequences. Also, naturally occurring inteins may display these properties and require no manipulation. Cleavage at the N- and/or C-terminus of an intein can occur uncontrollably or induced using nucleophilic compounds, such as thiol reagents, temperature, pH, salt, chaotropic agents, or any combination of the aforementioned conditions and/or reagents.

The Examples presented below are only intended as specific preferred embodiments of the present invention and are not intended to limit the scope of the invention except as provided in the claims herein. The present invention encompasses modifications and variations of the methods taught herein which would be obvious to one of ordinary skill in the art.

The references cited above and below are herein incorporated by reference.

EXAMPLE I

Creation of the Mth RIR1 Synthetic Gene

The gene encoding the Mth RIR1 intein along with 5 native N- and C-extein residues (Smith et al. supra (1997)) was constructed using 10 oligonucleotides (New England Biolabs, Beverly, Mass.) comprising both strands of the gene, as follows:

1) 5'-TCGAGGCAACCAACCCCTGCGTATCC GGT-GACACCATTGT AATGACTAGTGGCGGTC-CGCGCACTGTGGCTGAACTGGAG GGCAAACCGTTCACCGCAC-3' (SEQ ID NO:1)

2) 5'-CCGGTTGGCTGCTCGCCACAGTTGTGT ACAATGAAGCCAT TAGCAGTGAATGCGCTAG-CACCGTAAACAGTAGCGTCATA AACATCCTGGCGG-3' (SEQ ID NO:2)

3) 5'-pTGATTCGCGGCTCTGGCTACCCATGCC CCT-CAGGTTTCTT CCGCACCTGTGAACGTGACG-TATATGATCTGCGTACACGT GAGGGTCATTGCTTACGTTT-3' (SRQ ID NO:3)

4) 5'-pGACCCATGATCACCGTGTTCTGGTGA TGGATGGTGGCCTG GAATGGCGTGC-CGCGGGTGAACTGGAACGCGGCGACCGCC TGGTGATGGATGATGCAGCT-3' (SEQ ID NO:4)

5) 5'-pGGCGAGTTTCCGGCACTGGCAACCTT CCGTGGCCTGCGTG GCGCTGGCCGCCAGGAT-GTTTATGACGCTACTGTTTTACGG TGCTAGC-3' (SEQ ID NO:5)

6) 5'-pGCATTCACTGCTAATGGCTTCATTGTAC ACAACTGTGGCG AGCAGCCAA-3' (SEQ ID NO:6)

7) 5' pCCAGCGCCACGCAGGCCACGGAAGGT-TGCCAGTGCCGGAA ACTCGCCAGCTGCAT-CATCCATCACCAGGCGGTCGCCGCG TTCCAGTTCACCCGCGGCAC-3' (SEQ ID NO:7)

8) 5'-pGCCATTCCAGGCCACCATCCATCACC AGAACACGGTGATC ATGGGTCAAACGTAAG-CAATGACCCTCACGTGTACGCAGA TCATATACGT-3' (SEQ ID NO:8)

9) 5'-pCACGTTCACAGGTGCGGAAGAAACC TGAGGGGCATGGGTA GCCAGAGCCGCGAAT-CAGTGCGGTGAACGGTTTGCCCTCC AGTTCAGCCACAGTGCG-3' (SEQ ID NO:9)

10) 5'-pCGGACCGCCACTAGTCATTACAATGGT GTCACCGGATACG CAGGGGTTGGTTGCC-3' (SEQ ID NO:10)

To ensure maximal E. coli expression, the coding region of the synthetic Mth RIR1 intein incorporates 61 silent base mutations in 49 of the 134 codons (see FIG. 4) in the wildtype Mth RIR1 intein gene (GenBank AE000845). The oligonucleotides were annealed by mixing at equimolar ratios (400 nM) in a ligation buffer (50 mM Tris-HCl, pH 7.5 containing 10 mM $MgCl_2$, 10 mM dithiothreitol, 1 mM ATP, and 25 μg BSA) followed by heating to 95° C. After cooling to room temperature, the annealed and ligated oligonucleotides were inserted into the XhoI and AgeI sites of pMYB5 (NEB), replacing the Sce VMA intein and creating the plasmid pMRB8P.

Engineering the Mth RIR1 Intein for N- and C-terminal Cleavage

The unique XhoI and SpeI sites flanking the N-terminal splice junction and the unique BsrGI and AgeI sites flanking the C-terminal splice junction allowed substitution of amino acid residues by linker replacement. The proline residue, Pro$^{-1}$, preceding the intein in pMRB8P was substituted with alanine or glycine to yield pMRB8A and pMRB8G1, respectively. Substitution of Pro$^{-1}$-Cys$^1$ with Gly-Ser or Gly-Ala yielded pMRB9GS and pMRB9GA, respectively. Replacing Asn$^{134}$ with Ala in pMRB8G1 resulted in PMRB10G. The following linkers were used for substitution of the native amino acids at the splice junctions (each linker was formed by annealing two synthetic oligonucleotides as described above):

| | |
|---|---|
| P$^{-1}$A linker: | 5'-TCGAGGCAACCAACGCATGCGTATCCGGT GACACCATTGTAATGA-3' (SEQ ID NO:11) |
| and | 5'-CTAGTCATTACAATGGTGTCACCGGATAC GCATGCGTTGGTTGCC-3' (SEQ ID NO:12) |
| P$^{-1}$G linker: | 5'-TCGAGGGCTGCGTATCCGGTGACACCATT GTAATGA-3 (SEQ ID NO:13)' |
| and | 5'-CTAGTCATTACAATGGTGTCACCGGATAC GCAGCCC-3' (SEQ ID NO:14) |
| P$^{-1}$G/C$^1$S linker: | 5'-TCGAGGGCATCGAGGCAACCAACGGATC CGTATCCGGTGACACCATTGTAATGA-3' (SEQ ID NO:15) |
| and | 5'-CTAGTCATTACAATGGTGTCACCGGATAC GGATCCGTTGGTTGCCTCGATGCCC-3' (SEQ ID NO:16) |
| P$^{-1}$G/C$^1$A linker: | 5'-TCGAGGGCATCGAGGCAACCAACGGCGCC GTATCCGGTGACACCATTGTAATGA-3' (SEQ ID NO:17) |
| and | 5'-CTAGTCATTACAATGGTGTCACCGGATAC GGCGCCGTTGGTTGCCTCGATGCCC-3' (SEQ ID NO:18) |
| N$^{134}$A linker: | 5'-GTACACGCATGCGGCGAGCAGCCCGG GA-3' (SEQ ID NO:19) |
| and | 5'-CCGGTCCCGGGCTGCTCGCCGCATGC GT-3' (SEQ ID NO:20) | pBRL-A was constructed by substituting the *Escherichia coli* maltose binding protein (MBP) and the *Bacillus circulans* chitin binding domain (CBD) coding regions in pMRB9GA with the CBD and the T4 DNA ligase coding regions, respectively, subcloned from the pBYT4 plasmid.

EXAMPLE II

Generating a Thioester-tagged Protein

The pMRB10G construct from Example I contains the Mth RIR1 intein engineered to undergo thiol reagent induced cleavage at the N-terminal splice junction (FIG. 1, N-terminal cleavage) and was used to isolate proteins with a C-terminal thioester as described previously for the Sce VMA and Mxe GyrA inteins (Chong et al. supra 1997); Evans et al., supra (1998)). Briefly, ER2566 cells (Evans et. al. (1998)) containing the appropriate plasmid were grown at 37° C. in LB 20 broth containing 100 μg/mL ampicillin to an OD$_{600}$ of 0.5–0.6 followed by induction with IPTG (0.5 mM). Induction was either overnight at 15° C. or for 3 hours at 30° C.

The cells were pelleted by centrifugation at 3,000×g for 30 minutes followed by resuspension in buffer A (20 mM Tris-HCl, pH 7.5 containing 500 mM NaCl). The cell contents were released by sonication. Cell debris was removed by centrifugation at 23,000×g for 30 minutes and the supernatant was applied to a column packed with chitin resin (10 mL bed volume) equilibrated in buffer A. Unbound protein was washed from the column with 10 column volumes of buffer A.

Thiol reagent-induced cleavage was initiated by rapidly equilibrating the chitin resin in buffer B (20 mM Tris-HCl, pH 8 containing 500 mM NaCl and 100 mM 2-mercaptoethane-sulfonic acid (MESNA)). The cleavage reaction, which simultaneously generates a C-terminal thioester on the target protein, proceeded overnight at 4° C. after which the protein was eluted from the column. The use of the pMRB10G construct resulted in the isolation of MBP with a C-terminal thioester (FIG, 2A).

Isolating Proteins with an N-terminal Cysteine

The pBRL-A construct from Example I contains an Mth RIR1 intein engineered to undergo controllable cleavage at its C-terminus, and was used to purify proteins with an N-terminal cysteine (FIG. 1, C-terminal cleavage). The expression and purification protocol was performed as described in Example II, except with buffer A replaced by buffer C (20 mM Tris-HCl, pH 8.5 containing 500 mM NaCl) and buffer B replaced by buffer D (20 mM Tris-HCl, pH 7.0 containing 500 mM NaCl). Also, following equilibration of the column in buffer D the cleavage reaction proceeded overnight at room temperature.

The expression of plasmid pBRL-A resulted in the purification of 4-6 mg/L cell culture of T4 DNA ligase possessing an N-terminal cysteine (FIG. 2A). Protein concentrations were determined using the Bio-Rad protein assay (Bio-Rad Laboratories, Inc., Hercules, Calif.).

EXAMPLE III

Protein-protein Ligation using Intein-mediated Protein Ligation

Intein-mediated protein ligation (IPL) was used to fuse two proteins (FIG. 2B). Freshly isolated thioester-tagged protein from Example II was mixed with freshly isolated protein containing an N-terminal cysteine residue from Example II, with typical starting concentrations of 1–200 μM. The solution was concentrated with a Centriprep 3 or Centriprep 30 apparatus (Millipore Corporation, Bedford, Mass.) then with a Centricon 3 or Centricon 10 apparatus to a final concentration of 0.15–1.2 mM for each protein.

Ligation reactions proceeded overnight at 4° C. and were visualized using SDS-PAGE with 12% Tris-glycine gels (Novex Experimental Technology, San Diego, Calif.) stained with Coomassie Brilliant Blue. Typical ligation efficiencies ranged from 20–60%.

Confirmation of Ligation in IPL Reactions

A Factor Xa site in MBP that exists 5 amino acids N-terminal from the site of fusion (Maina et al, supra (1988)) allowed amino acid sequencing through the ligation junction. The sequence obtained was NH$_2$-TLEGCGEQPTGXLK-COOH (SEQ ID NO:21) which matched the last 4 residues of MBP (TLEG) followed by a linker sequence (CGEQPTG (SEQ ID NO:22)) and the start of T4 DNA ligase (ILK). During amino acid sequencing, the cycle expected to yield an isoleucine did not have a strong enough signal to assign it to a specific residue, so it was represented as an X. The cysteine was identified as the acrylamide alkylation product.

The Factor Xa proteolysis was performed on 2 mg of ligation reaction involving MBP and T4 DNA ligase. This reaction mixture was bound to 3 mL of amylose resin (New England Biolabs, Inc., Beverly, Mass.) equilibrated in buffer A (see Example II). Unreacted T4 DNA ligase was rinsed from the column with 10 column volumes of buffer A. Unligated MBP and the MBP-T4 DNA ligase fusion protein were eluted from the amylose resin using buffer E (20 mM Tris-HCl, pH 7.5 containing 500 mM NaCl and 10 mM maltose). Overnight incubation of the eluted protein with a 200:1 protein:bovine Factor Xa (NEB) ratio (w/w) at 4° C. resulted in the proteolysis of the fusion protein and regeneration of a band on SDS-PAGE gels that ran at a molecular weight similar to T4 DNA ligase. N-terminal amino acid sequencing of the proteolyzed fusion protein was performed on a Procise 494 protein sequencer (PE Applied Biosystems, Foster City, Calif.).

Temperature Sensitivity of the Mth RIR1 Intein

The cleavage and/or splicing activity of the Mth RIR1 intein was more proficient when protein synthesis was induced at 15° C. than when the induction temperature was raised to 37° C. (FIG. 3). The effect temperature has on the Mth RIR1 represents a way to control the activity of this intein for use in controlled splicing or cleavage reactions. Replacement of Pro$^{-1}$ with a Gly and Cys$^{1}$ with a Ser resulted in a double mutant, the pMRB9GS construct, which showed only in vivo C-terminal cleavage activity when protein synthesis was induced at 15° C. but not at 37° C. Another double mutant, the pMRB9GA construct, displayed slow cleavage, even at 15° C., which allowed the accumulation of substantial amounts of the precursor protein and showed potential for use as a C-terminal cleavage construct for protein purification.

What is claimed is:

1. A method for generating a cysteine or a selenocysteine at the N-terminus of a target protein, comprising:
   expressing in a host cell, a nucleic acid encoding a fusion protein comprising an intein and a target protein wherein the intein-encoding sequence is 5'-proximal to a codon specifying a cysteine or a selenocysteine at the amino terminus of the target protein; and
   cleaving the intein from the target protein so as to generate the cysteine or selenocysteine at the N-terminus of the target protein.

2. A method for ligating target proteins comprising the steps of:
   (a) expressing from a first plasmid in a first host cell, a first fusion protein comprising a first target protein having a C-terminus fused to an intein or modification thereof;
   (b) expressing from a second plasmid in the first host cell or a second host cell, a second fusion protein comprising a second target protein having an N-terminal cysteine or selenocysteine fused to an intein or modification thereof;
   (c) obtaining an extracellular preparation of the first fusion protein and an extracellular preparation of the second fusion protein;
   (d) adding a thiol reagent to the extracellular preparation of the first fusion protein whereby the first intein is cleaved so as to form a C-terminal thioester on the first target protein;
   (e) cleaving the second intein or modification thereof from the second target protein in the extracellular preparation of the second fusion protein and forming an N-terminal cysteine or selenocysteine on the second target protein; and
   (f) permitting ligation of the first target protein with the C-terminal thioester with the second target protein of step (e).

3. The method of claim 2, wherein the first intein is the Mth RIR1 intein depicted in SEQ ID NO:24, or a modified form of the Mth RIR1 intein.

4. The method of claim 2, wherein the second intein is the Mth RIR1 intein depicted in SEQ ID NO:24, or a modified form of the Mth RIR1 intein.

5. The method of claim 3 or 4, wherein the modification of the Mth RIR1 intein comprises a substitution of alanine for the asparagine at position 134 at the C-terminus or a substitution of alanine or serine for the cysteine at position 1 at the N-terminus.

6. The method of claim 2, wherein the second target protein of step (e) is cleaved from the second intein in the presence of a thiol reagent or by modulating any of temperature, pH, salt, chaotropic agents or combinations thereof.

7. The method of claim 2, wherein step (c) further comprises purifying the first or second fusion protein from the extracellular preparation.

8. The method of claim 7, wherein the step of purifying the fusion protein further comprises binding to a chitin resin column.

9. The method of claim 2, wherein the first and second plasmids are capable of expression in a host cell selected from the group consisting of a bacterial, a yeast, a plant, an insect and a mammalian host cell.

10. A method for ligating a first and a second target protein, comprising:
   (a) inducing cleavage of a first intein or modification thereof from a fusion protein comprising the intein and a first target protein, to form an N-terminus cysteine or selenocysteine amino acid on the target protein;
   (b) combining in a mixture the first target protein of (a) with a second target protein having a C-terminus thioester; and
   (c) ligating the first and second target proteins.

11. A method for cyclization of a target protein having an N-terminal cysteine or a selenocysteine, the method comprising the steps of:
   (a) expressing from a plasmid in a host cell, a fusion protein comprising a target protein having either a cysteine or a selenocysteine at the N-terminus, and two inteins, wherein the first intein, or a modification thereof, is fused to the C-terminus of the target protein and the second intein, or modification thereof, is fused to the N-terminal cysteine or selenocysteine of the target protein;
   (b) obtaining an extracellular preparation of the expressed fusion protein;
   (c) inducing cleavage of the fusion protein, comprising addition of a thiol reagent, to remove the first and second inteins from the target protein thereby obtaining the target protein having a C-terminal thioester and an N-terminal cysteine or selenocysteine; and
   (d) permitting intramolecular ligation of the N-terminus of the target protein to the C-terminus of the target protein thereby forming a cyclized protein.

12. The method of claim 11, wherein the intein is the Mth RIR1 intein depicted in SEQ ID NO:24, or a modified form of the Mth RIR1 intein wherein the modification comprises a substitution of alanine for the asparagine at position 134 at the C-terminus or a substitution of alanine or serine for the cysteine at position 1 at the N-terminus.

13. The method of claim 11, wherein (i) modulation of any of temperature, pH, salt, the concentration of chaotropic agents or combinations thereof cleaves the intein or modification thereof from the target protein to form the N-terminal cysteine or selenocysteine, and (ii) the addition of the thiol reagent forms the C-terminal thioester on the target protein.

14. The method of claim 11, wherein step (b) further comprises: purifying the fusion protein from the extracellular preparation.

15. The method of claim 11, wherein the step of purifying the fusion protein further comprising binding to a chitin resin column.

16. The method of claim 11, wherein the plasmid is capable of expression in a host cell selected from the group consisting of a bacterial, a yeast, a plant, an insect and a mammalian host cell.

17. A method for cyclization of a target protein having an N-terminal cysteine or selenocysteine, comprising:
   adding a thiol reagent to a fusion protein comprising a target protein having an N-terminal cysteine or selenocysteine and an intein, or modification thereof, fused to the C-terminus of the target protein in order to induce cleavage of the intein from the target protein and the formation of a C-terminal thioester on the target protein; and
   permitting intramolecular ligation of the N-terminus of the C-terminal thioester of the target protein to the N-terminal cysteine or selenocysteine of the target protein for cyclization of the target protein.

18. A method for forming a polymer by intermolecular ligation between target proteins in a preparation, the method comprising the steps of:
   (a) forming each target protein having a C-terminal thioester and an N-terminal cysteine or selenocysteine by cleaving a first and second intein or modifications thereof from a fusion protein, the fusion protein comprising a target protein fused to the first intein at the C-terminal end and the second intein at the N-terminal end; and
   (b) allowing intermolecular litigation between target proteins by reacting the C-terminal thioester of one target protein with the N-terminal cysteine or selenocysteine at the, N-terminus of another target protein to form a polymer.

19. The method of claim 18, wherein the first intein is the Mth RIR1 intein depicted in SEQ ID NO:24, or a modified form of the Mth RIR1 intein.

20. The method of claim 18, wherein the second intein is the Mth RIR1 intein depicted in SEQ ID NO:24, or a modified form of the Mth RIR1 intein.

21. The method of claim 19 or 20, wherein the modification of the Mth RIR1 intein comprises a substitution of alanine for the asparagine at position 134 at the C-terminus or a substitution of alanine or serine for the cysteine at position at position 1 at the N-terminus.

22. The method of claim 18, wherein the second intein is cleaved from the target protein by modulating temperature, pH, salt or chaotropic agents or combinations thereof.

23. The method of claim 18, wherein the fusion protein is expressed by a plasmid which is capable of expression in a host cell selected from the group consisting of a bacterial, a yeast, a plant, an insect and a mammalian host cell.

24. A modified Mth RIR1 intein, wherein the intein comprising the amino acid sequence depicted in SEQ ID NO:24 comprises a substitution of alanine for the asparagine at position 134 at the C-terminus of the intein or a substitution of alanine or serine for the cysteine at position 1 at the N-terminus of the intein.

* * * * *

SEQUENCE LISTING

```
<160> NUMBER OF SEQ ID NOS: 26

<210> SEQ ID NO 1
<211> LENGTH: 99
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 1
tcgaggcaac caacccctgc gtatccggtg acaccattgt aatgactagt ggcggtccgc      60
gcactgtggc tgaactggag ggcaaaccgt tcaccgcac                             99

<210> SEQ ID NO 2
<211> LENGTH: 93
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 2
ccggttggct gctcgccaca gttgtgtaca atgaagccat tagcagtgaa tgcgctagca      60
ccgtaaacag tagcgtcata aacatcctgg cgg                                   93

<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 3
tgattcgcgg ctctggctac ccatgcccct caggtttctt ccgcacctgt gaacgtgacg      60
tatatgatct gcgtacacgt gagggtcatt gcttacgttt                            100

<210> SEQ ID NO 4
<211> LENGTH: 100
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 4
```

```
gacccatgat caccgtgttc tggtgatgga tggtggcctg gaatggcgtg ccgcgggtga    60
actggaacgc ggcgaccgcc tggtgatgga tgatgcagct                         100
```

<210> SEQ ID NO 5
<211> LENGTH: 87
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 5

```
ggcgagtttc cggcactggc aaccttccgt ggcctgcgtg cgctggccg ccaggatgtt     60 tatgacgcta ctgtttacgg tgctagc                                       87
```

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 6

```
gcattcactg ctaatggctt cattgtacac aactgtggcg agcagccaa                49
```

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 7

```
ccagcgccac gcaggccacg gaaggttgcc agtgccggaa actcgccagc tgcatcatcc    60
atcaccaggc ggtcgccgcg ttccagttca cccgcggcac                         100
```

<210> SEQ ID NO 8
<211> LENGTH: 90
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 8

```
gccattccag gccaccatcc atcaccagaa cacggtgatc atgggtcaaa cgtaagcaat    60
gaccctcacg tgtacgcaga tcatatacgt                                    90
```

<210> SEQ ID NO 9
<211> LENGTH: 97
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 9

```
cacgttcaca ggtgcggaag aaacctgagg ggcatgggta gccagagccg cgaatcagtg    60
cggtgaacgg tttgccctcc agttcagcca cagtgcg                            97
```

```
<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 10
cggaccgcca ctagtcatta caatggtgtc accggatacg caggggttgg ttgcc          55

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 11
tcgaggcaac caacgcatgc gtatccggtg acaccattgt aatga                     45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 12
ctagtcatta caatggtgtc accggatacg catgcgttgg ttgcc                     45

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 13
tcgagggctg cgtatccggt gacaccattg taatga                               36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 14
ctagtcatta caatggtgtc accggatacg cagccc                               36

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 15
tcgagggcat cgaggcaacc aacggatccg tatccggtga caccattgta atga           54

<210> SEQ ID NO 16
```

```
<211> LENGTH: 54
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 16
ctagtcatta caatggtgtc accggatacg gatccgttgg ttgcctcgat gccc          54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 17
tcgagggcat cgaggcaacc aacggcgccg tatccggtga caccattgta atga          54

<210> SEQ ID NO 18
<211> LENGTH: 54
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 18
ctagtcatta caatggtgtc accggatacg gcgccgttgg ttgcctcgat gccc          54

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 19
gtacacgcat gcggcgagca gcccggga                                       28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 20
ccggtcccgg gctgctcgcc gcatgcgt                                       28

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Chemically
      Synthesized From Methanobacterium thermoautotrophicum.
<220> FEATURE:
<223> OTHER INFORMATION: At position 12, "Xaa" = any amino acid

<400> SEQUENCE: 21

Thr Leu Glu Gly Cys Gly Glu Gln Pro Thr Gly Xaa Leu Lys
 1               5                  10
```

```
<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 22

Cys Gly Glu Gln Pro Thr Gly
  1               5

<210> SEQ ID NO 23
<211> LENGTH: 462
<212> TYPE: DNA
<213> ORGANISM: Artificial Sequence
<220> FEATURE:
<221> NAME/KEY: CDS
<222> LOCATION: (1)..(462)
<223> OTHER INFORMATION: Description of Artificial Sequence: Chemically
      Synthesized From Methanobacterium thermoautotrophicum.

<400> SEQUENCE: 23 caa ctc ggg agg ata gag gca acc aac ccc tgt gta tcc ggt gac acc       48
Gln Leu Gly Arg Ile Glu Ala Thr Asn Pro Cys Val Ser Gly Asp Thr
  1               5                  10                  15 att gta atg aca tcc ggg ggt ccg cgg aca gtg gct gaa ctg gag ggc       96
Ile Val Met Thr Ser Gly Gly Pro Arg Thr Val Ala Glu Leu Glu Gly
                 20                  25                  30 aag ccc ttc acc gca ctt atc agg ggc tca ggg tac ccc tgc ccc tca      144
Lys Pro Phe Thr Ala Leu Ile Arg Gly Ser Gly Tyr Pro Cys Pro Ser
             35                  40                  45 ggt ttc ttc agg acc tgt gaa cgg gac gta tat gat ctt aga acc agg      192
Gly Phe Phe Arg Thr Cys Glu Arg Asp Val Tyr Asp Leu Arg Thr Arg
         50                  55                  60 gag ggt cat tgc tta agg ttg acc cat gat cac agg gtc ctt gta atg      240
Glu Gly His Cys Leu Arg Leu Thr His Asp His Arg Val Leu Val Met
 65                  70                  75                  80 gat ggt ggt ctg gaa tgg cgt gcc gcc ggt gaa ctt gaa agg gga gac      288
Asp Gly Gly Leu Glu Trp Arg Ala Ala Gly Glu Leu Glu Arg Gly Asp
                 85                  90                  95 cgc ctt gtg atg gat gat gct gca ggg gag ttt ccg gca ctt gca acc      336
Arg Leu Val Met Asp Asp Ala Ala Gly Glu Phe Pro Ala Leu Ala Thr
            100                 105                 110 ttc aga ggc ctc agg ggc gcc ggc cgc cag gat gtc tat gac gcc act      384
Phe Arg Gly Leu Arg Gly Ala Gly Arg Gln Asp Val Tyr Asp Ala Thr
        115                 120                 125 gtc tac ggt gcc agt gca ttc aca gcc aat gga ttc ata gtc cac aac      432
Val Tyr Gly Ala Ser Ala Phe Thr Ala Asn Gly Phe Ile Val His Asn
    130                 135                 140 tgt ggg gag cag cca ctc ctc acc cat gaa                              462
Cys Gly Glu Gln Pro Leu Leu Thr His Glu
145                 150

<210> SEQ ID NO 24
<211> LENGTH: 154
<212> TYPE: PRT
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 24

Gln Leu Gly Arg Ile Glu Ala Thr Asn Pro Cys Val Ser Gly Asp Thr
```

```
                1               5                   10                  15
              Ile Val Met Thr Ser Gly Gly Pro Arg Thr Val Ala Glu Leu Glu Gly
                          20                  25                  30

Lys Pro Phe Thr Ala Leu Ile Arg Gly Ser Gly Tyr Pro Cys Pro Ser
                          35                  40                  45

Gly Phe Phe Arg Thr Cys Glu Arg Asp Val Tyr Asp Leu Arg Thr Arg
                          50                  55                  60

Glu Gly His Cys Leu Arg Leu Thr His Asp His Arg Val Leu Val Met
              65                  70                  75                  80

Asp Gly Gly Leu Glu Trp Arg Ala Ala Gly Glu Leu Glu Arg Gly Asp
                                  85                  90                  95

Arg Leu Val Met Asp Asp Ala Ala Gly Glu Phe Pro Ala Leu Ala Thr
                              100                 105                 110

Phe Arg Gly Leu Arg Gly Ala Gly Arg Gln Asp Val Tyr Asp Ala Thr
                          115                 120                 125

Val Tyr Gly Ala Ser Ala Phe Thr Ala Asn Gly Phe Ile Val His Asn
                      130                 135                 140

Cys Gly Glu Gln Pro Leu Leu Thr His Glu
              145                 150

<210> SEQ ID NO 25
<211> LENGTH: 447
<212> TYPE: DNA
<213> ORGANISM: Artificial Sequence
<220> FEATURE:
<221> NAME/KEY: CDS
<222> LOCATION: (1)..(447)
<223> OTHER INFORMATION: Description of Artificial Sequence: Chemically
      Synthesized From Methanobacterium thermoautotrophicum.

<400> SEQUENCE: 25 ctc gag gca acc aac ccc tgc gta tcc ggt gac acc att gta atg act      48
Leu Glu Ala Thr Asn Pro Cys Val Ser Gly Asp Thr Ile Val Met Thr
1               5                   10                  15 agt ggc ggt ccg cgc act gtg gct gaa ctg gag ggc aaa ccg ttc acc      96
Ser Gly Gly Pro Arg Thr Val Ala Glu Leu Glu Gly Lys Pro Phe Thr
            20                  25                  30 gca ctg att cgc ggc tct ggc tac cca tgc ccc tca ggt ttc ttc cgc     144
Ala Leu Ile Arg Gly Ser Gly Tyr Pro Cys Pro Ser Gly Phe Phe Arg
        35                  40                  45 acc tgt gaa cgt gac gta tat gat ctg cgt aca cgt gag ggt cat tgc     192
Thr Cys Glu Arg Asp Val Tyr Asp Leu Arg Thr Arg Glu Gly His Cys
    50                  55                  60 tta cgt ttg acc cat gat cac cgt gtt ctg gtg atg gat ggt ggc ctg     240
Leu Arg Leu Thr His Asp His Arg Val Leu Val Met Asp Gly Gly Leu
65                  70                  75                  80 gaa tgg cgt gcc gcg ggt gaa ctg gaa cgc ggc gac cgc ctg gtg atg     288
Glu Trp Arg Ala Ala Gly Glu Leu Glu Arg Gly Asp Arg Leu Val Met
                85                  90                  95 gat gat gca gct ggc gag ttt ccg gca ctg gca acc ttc cgt ggc ctg     336
Asp Asp Ala Ala Gly Glu Phe Pro Ala Leu Ala Thr Phe Arg Gly Leu
            100                 105                 110 cgt ggc gct ggc cgc cag gat gtt tat gac gct act gtt tac ggt gct     384
Arg Gly Ala Gly Arg Gln Asp Val Tyr Asp Ala Thr Val Tyr Gly Ala
        115                 120                 125 agc gca ttc act gct aat ggc ttc att gta cac aac tgt ggc gag cag     432
Ser Ala Phe Thr Ala Asn Gly Phe Ile Val His Asn Cys Gly Glu Gln
    130                 135                 140 cca acc ggt gaa ttc                                                 447
```

```
Pro Thr Gly Glu Phe
145

<210> SEQ ID NO 26
<211> LENGTH: 149
<212> TYPE: PRT
<213> ORGANISM: Artificial Sequence
<220> FEATURE:
<223> OTHER INFORMATION: Description of Artificial Sequence: Chemically
      Synthesized From Methanobacterium thermoautotrophicum.

<400> SEQUENCE: 26

Leu Glu Ala Thr Asn Pro Cys Val Ser Gly Asp Thr Ile Val Met Thr
1               5                   10                  15

Ser Gly Gly Pro Arg Thr Val Ala Glu Leu Glu Gly Lys Pro Phe Thr
            20                  25                  30

Ala Leu Ile Arg Gly Ser Gly Tyr Pro Cys Pro Ser Gly Phe Phe Arg
        35                  40                  45

Thr Cys Glu Arg Asp Val Tyr Asp Leu Arg Thr Arg Glu Gly His Cys
    50                  55                  60

Leu Arg Leu Thr His Asp His Arg Val Leu Val Met Asp Gly Gly Leu
65                  70                  75                  80

Glu Trp Arg Ala Ala Gly Glu Leu Glu Arg Gly Asp Arg Leu Val Met
                85                  90                  95

Asp Asp Ala Ala Gly Glu Phe Pro Ala Leu Ala Thr Phe Arg Gly Leu
            100                 105                 110

Arg Gly Ala Gly Arg Gln Asp Val Tyr Asp Ala Thr Val Tyr Gly Ala
        115                 120                 125

Ser Ala Phe Thr Ala Asn Gly Phe Ile Val His Asn Cys Gly Glu Gln
    130                 135                 140

Pro Thr Gly Glu Phe
145
```